United States Patent
Lee et al.

(10) Patent No.: US 10,156,542 B2
(45) Date of Patent: Dec. 18, 2018

(54) PULSE OPERATING METHOD FOR FET-TYPE SENSOR HAVING HORIZONTAL FLOATING GATE

(71) Applicant: SEOUL NATIONAL UNIVERSITY R&DB FOUNDATION, Seoul (KR)

(72) Inventors: Jong-Ho Lee, Seoul (KR); Jongmin Shin, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 53 days.

(21) Appl. No.: 15/612,384

(22) Filed: Jun. 2, 2017

(65) Prior Publication Data

US 2017/0350852 A1 Dec. 7, 2017

Related U.S. Application Data

(60) Provisional application No. 62/345,194, filed on Jun. 3, 2016.

(51) Int. Cl.
*G01N 27/414* (2006.01)
*G01N 27/16* (2006.01)
(Continued)

(52) U.S. Cl.
CPC ....... *G01N 27/4141* (2013.01); *G01N 27/002* (2013.01); *G01N 27/16* (2013.01);
(Continued)

(58) Field of Classification Search
CPC .... B60T 13/686; B60T 13/148; B60T 13/142; B60T 13/662
See application file for complete search history.

(56) References Cited

U.S. PATENT DOCUMENTS

| | | | | | |
|---|---|---|---|---|---|
| 2010/0193375 | A1* | 8/2010 | Liemersdorf | ...... | G01N 27/4141 205/775 |
| 2015/0323482 | A1* | 11/2015 | Shimoyama | ....... | G01N 27/4146 73/31.06 |

FOREIGN PATENT DOCUMENTS

| KR | 20130052528 | 5/2013 |
|---|---|---|
| KR | 20140106335 | 9/2014 |

OTHER PUBLICATIONS

Hong, et al., Highly selective ZnO gas sensor based on MOSFET having a horizontal floating-gate, Sensors and Actuators B: Chemical, 2016, pp. 653-659.

(Continued)

*Primary Examiner* — Alesa Allgood
*Assistant Examiner* — Zannatul Ferdous
(74) *Attorney, Agent, or Firm* — Cantor Colburn LLP

(57) ABSTRACT

Provided is a pulse operating method for an FET-type sensor having a horizontal floating electrode. The pulse operating method for an FET-type sensor includes a reading preparation step of applying one or more pre-bias voltage pulses ($V_{pre}$) to the control electrode and a reading step of applying one or more read-bias voltage pulses ($V_{rCG}$) to the control electrode and applying a voltage pulse ($V_{rDs}$) synchronized with the read-bias voltage pulse between a drain and a source. The reactivity and the recovery time can be improved according to the width or the magnitude of the pre-bias voltage pulse applied to the input terminal of the control electrode, and the oxidizing gas and the reducing gas can be distinguished. In addition, since current flows to the FET-type sensor only in the read-biasing period, power consumption can be greatly reduced.

19 Claims, 23 Drawing Sheets

(51) Int. Cl.
  *G01N 27/00* (2006.01)
  *G01N 33/00* (2006.01)
  *H01L 29/423* (2006.01)
  *H01L 29/788* (2006.01)

(52) U.S. Cl.
  CPC ... *G01N 33/0031* (2013.01); *H01L 29/42328* (2013.01); *H01L 29/788* (2013.01)

(56) References Cited

OTHER PUBLICATIONS

Shin, et al., Highly Improved Response and Recovery Characteristics of Si FET-type Gas Sensor Using Pre-bias, International Electron Device Meeting, 2016, pp. 1-4.

* cited by examiner

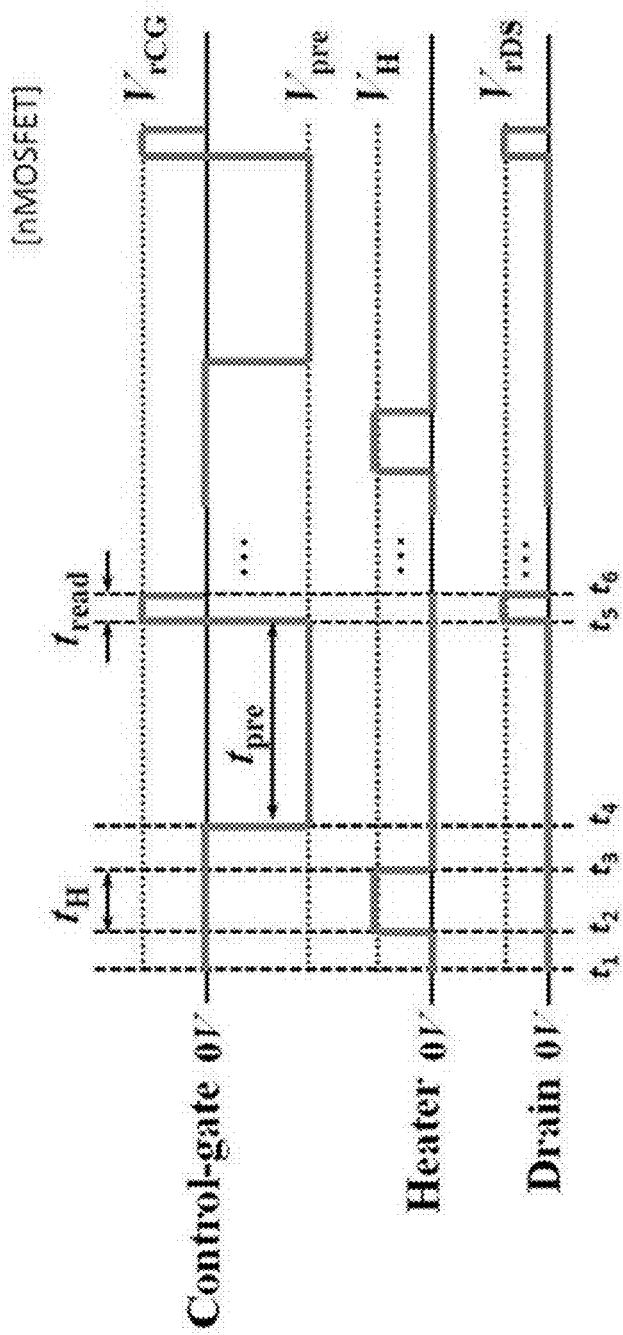

PULSE OPERATING METHOD FOR FET-TYPE SENSOR HAVING HORIZONTAL FLOATING GATE

BACKGROUND OF THE INVENTION

1. Field of the Invention

The present invention relates to a pulse operating method for a sensor, and more particularly, to a sensor operating method of applying a pre-bias voltage pulse to an FET (Field Effect Transistor)-type sensor having a floating gate formed in a horizontal direction to be capable of improving sensitivity and recovery characteristics of the sensor and allowing the sensor to operate with low power.

2. Description of the Related Art

In recent years, as the demand for sensors is increased, various types of sensors have been developed. Among these sensors, FET (Field Effect Transistor) sensors having a floating gate with high input impedance and high amplification rate have been researched. In addition, as low power and high sensitivity due to nigh transconductance and incorporation with existing CMOS circuits are required, FET-type sensors have been increasingly researched.

Korean Patent Laid-open Publication Ho. 2013-52528 (Patent Document 1) relates to an "FET-type gas sensor having a horizontal floating gate". In Patent Document 1, disclosed is an FET-type gas sensor where a control electrode and a floating electrode are formed in a horizontal direction with a sensing material layer interposed therebetween in order to solve problems occurring in the existing FET-type sensors where a control electrode, a floating electrode, and a sensing layer are formed in a vertical direction. The problems occurring in the existing FET-type sensors are a low coupling ratio between the control electrode and the floating electrode, low sensitivity, and high power consumption caused from limitation in selecting a sensing material and a parasitic capacitance component and high manufacturing cost caused from process complexity. In addition, several sensing mechanisms depending on a structure of the sensor are disclosed, and arrays including a plurality of gas sensors operating with the sensing mechanisms are also disclosed.

FIGS. 1A to 1D are cross-sectional views of an FET-type gas sensor having a horizontal floating electrode capable of sensing a change in work function as disclosed in Patent Document 1. Since a control electrode is directly electrically connected to a sensing material layer, a voltage of the sensing material layer is changed together with a voltage of the control electrode according to a change in voltage of the control electrode. When the work function of the sensing material layer reacting with a specific gas is changed, the work function of the control electrode is changed. Therefore, the voltage to be transferred to the floating electrode is changed, and channel formation and channel resistance of the semiconductor body are affected. By using this point, the specific gas is sensed with a current flowing through source and drain electrodes.

FIGS. 2A and 2B are a plan view and a cross-sectional view of an FET-type gas sensor having a horizontal floating electrode capable of sensing a change in work function and a change in capacitance disclosed in Patent Document 1. Unlike the gas sensor disclosed in FIGS. 1A to 1D, the control electrode and the sensing material layer are formed to be separated from each other with an insulating material interposed therebetween. Accordingly, the voltage of the control electrode is transferred to the sensing material, layer by the capacitance of the control electrode and the sensing material layer, and the voltage of the floating electrode is determined by the capacitance of the sensing material layer and the floating electrode.

The sensing material layer reacts with a specific gas to change a dielectric constant or a work function, so that a voltage to be transferred to the floating electrode is changed. Therefore, by using the characteristic that the channel formation and the channel resistance of the semiconductor body are affected, it is sensed by a change in current flowing through the source and drain electrodes.

FIGS. 5A to 5C illustrate cross-sectional views of an FET-type gas sensor that can be used as a heater by applying a voltage across a first electrode. An air layer is formed with a certain depth in the semiconductor substrate below the first electrode and the sensing material layer, and thus, heat is prevented from being released through the semiconductor substrate having high thermal conductivity, so that it is possible to effectively transfer heat to the sensing material layer. By applying a predetermined voltage to both ends of the first electrode, a current flows to generate heat, so that it is possible to improve reactivity between the sensing material layer and a gas.

Korean Patent Laid-Open Publication No. 2014-106335 (Patent Document 2) relates to a "three-dimensional Fin-FET-type gas sensor having a horizontal floating gate". In Patent Document 2, similarly to Patent Document 1, disclosed is a three-dimensional Fin-FET-type gas sensor where s floating electrode is formed to surround a semiconductor body protruding in a FIN shape to enlarge a width of a channel to increase a drain current, so that, the Fin-FET-type gas sensor has an advantage of increasing the sensitivity of the sensor.

Non-Patent Document 1 is "Highly selective ZnO gas sensor based on MOSFET having a horizontal floating-gate, Sensors and Actuator B", Y. Hong et al., Chemical, 232, p 653, 2016. In Non-Patent Document 1 gas reaction is sensed by using an FET-type gas sensor where a control electrode and a floating electrode are formed in a horizontal direction with a sensing material layer interposed therebetween to sense a change in work function disclosed in Patent Document 1. When an oxidizing and a reducing gas react with the sensing material layer, the work function of the sensing material layer is changed. As a result, a threshold voltage of the FET-type gas sensor is changed, and thus, a change in drain current is sensed. A certain read voltage (read-bias voltage pulse is applied to the gate, source, and drain to check gas reactivity caused from a change in source/drain current according to presence or absence of gas adsorption. However, when a constant voltage (DC voltage) is applied in the measurement of the gas reaction in the FET-type gas sensor, the drain current continues to flow, and thus, stress and power consumption of the gas sensor is increased.

Non-Patent Document 2 is "Highly improved response and recovery characteristics of Si FET-type gas sensor using pre-bias", J. Shin et al., International Electron Device Meeting. In Non-Patent Document 2, as an example of a pulse operating method for an FET-type gas sensor having a horizontal floating gate according to the invention, the reactivity and the recovery time of the sensor is greatly improved in comparison with the result of the measurement through the DC voltage application in Non-Patent Document 1. By applying a negative pre-bias voltage pulse to the control electrode, the reaction of $NO_2$ as an oxidative gas is improved, and by applying a positive pre-bias voltage pulse, the recovery time is greatly reduced due to facilitation of desorption of the oxidizing gas. The source voltage is always maintained at 0 V, and the pulse applied to the drain electrode is synchronized with the pulse applied to the control electrode. The source voltage is always maintained at 0 V, and while the pre-bias voltage pulse is applied to the control electrode, a voltage of 0 V is applied to the drain electrode to prevent a current from flowing in the gas sensor, so that power consumption is reduced.

Accordingly, the invention proposes a pulse operating method for an FET-type gas sensor having a horizontal floating electrode and a sensor array manufactured by using the FET-type gas sensor capable of improving gas reaction and recovery characteristics and reducing power consumption. In addition, the invention proposes a biasing method capable of effectively operating locally-implemented heaters by using characteristics of voltage pulse application.

SUMMARY OF THE INVENTION

The invention is to a pulse operating method for an FET-type sensor having a floating gate formed in a horizontal direction capable of reducing power consumption, improving sensitivity, and reducing recovery time in comparison with an FET-type sensor having a floating gate formed in a horizontal direction in the related art.

According to a first aspect of the invention, in a pulse operating method for an FET-type sensor where a sensing material layer is formed between a control electrode and a floating electrode, voltage pulses are applied to the control electrode, wherein a positive or negative pre-bias voltage pulse ($V_{pre}$) and a read-bias voltage pulse are applied, in combination of magnitudes, widths, order, and numbers of the pulses. A drain voltage is applied in synchronization with the read-bias voltage pulse applied to the control electrode, and while the pre-bias voltage pulse is applied, a voltage between a source and a drain is preferably maintained at 0 V, so that no current flows in the sensor.

In the pulse operating method for an FET-type sensor according to the first aspect of the invention, in the case where the pulse operating method is applied to a gas sensor, when a negative pre-bias voltage pulse is applied to a control electrode, adsorption of an oxidizing gas and desorption of a reducing gas can be facilitated. On the other hand, when a positive pre-bias voltage pulse is applied, desorption of an oxidizing gas and adsorption of a reducing gas can be facilitated.

The pre-bias voltage pulse and the read-bias voltage pulse may be alternately applied to the control electrode or at least one pre-bias voltage pulse may be applied and then at least one read-bias voltage pulse may be applied.

In the pulse operating method according to the first aspect, the reactivity and the recovery characteristic of the sensor can be improved by applying the different magnitude of the pre-bias voltage pulse to the control electrode.

It is preferable that the voltage applied to the control electrode is applied immediately after the pre-biasing. When the width of the voltage is minimized, it is possible to reduce power consumption.

In a pulse operating method for an FET-type sensor having a built-in heater according to the second aspect of the invention, a voltage for heating, a pre-bias voltage pulse, and a read-bias voltage pulse are applied to an input terminal of the control electrode, and therein, the voltage are applied in combination of magnitudes, widths, order, and numbers of the voltages.

In the case where the above-described pulse operating method according to the second aspect of the invention is applied to a gas sensor having a built-in heater and a combination of pulses fox heating, pre-bias, and read-bias is applied to the control electrode, adsorption or desorption of a specific gas to a sensing material layer can be facilitated, and thus, gas reactivity can be improved.

In the pulse operating method for a sensor array including a plurality of sensors operating as sensing mechanisms, negative or positive pre-bias voltage pulses can be applied to a plurality of the control electrodes, and the magnitudes and widths of the pulses applied can be different. Herein, read operation may be performed at a time by using the voltages applied to a plurality of the drain electrodes of a plurality of the sensors, or read operation may be performed by sequentially applying drain pulses.

In the pulse operating method for an FET-type sensor array including a plurality of FET-type sensors having a built-in heater according to the invention, heat-bias voltage pulses, pre-bias voltage pulses, and read-bias voltage pulses can be applied to the control electrode in combination of magnitudes, widths, order, and numbers of the pulses, and voltages for operations of the heater can be applied differently in magnitude and time depending on the sensing material layer.

In the case where the pulse operating method according to the invention is applied to an FET-type sensor including a control electrode, a sensing material layer, and a floating electrode disclosed in Patent Document 1, it is possible to achieve high reactivity, short recovery time, and low power consumption in comparison with the case disclosed in Non-Patent Document 1 where reaction is measured by using a constant DC voltage. In the invention, the reactivity and the recovery time can be improved according to the width or the magnitude of the pre-bias voltage pulse applied to the input terminal of the control electrode, and the oxidizing gas and the reducing gas can be distinguished in the case of application to the gas sensor.

The pulse operating method according to the invention can also be applied to an FET-type sensor having a built-in heater. By applying heat-bias voltage pulses for the heater, pre-bias voltage pulses, and read-bias voltage pulses are applied in combination of magnitudes, widths, order, and numbers of the pulses, so that it is possible to improve reactivity and recovery characteristics. In addition, since no current does flow in the gas sensor in the pre-biasing and heat-biasing periods except for the read-biasing period, power consumption can be reduced, so that the invention can be applied to low-power, mobile products.

BRIEF DESCRIPTION OF THE DRAWINGS

FIG. 1A is a plan view, FIG. 1B is a cross-sectional view taken along line A-A' in FIG. 1A, FIG. 1D is a cross-sectional view taken along line B-B' in FIG. 1A, and FIG. 1C is a cross-sectional view of a three-dimensional Fin-FET-type sensor as a modified form of FIG. 1B;

FIG. 2A is a plan view, and FIG. 2B is a cross-sectional view taken along line A-A' in FIG. 2A;

FIGS. 6A to 6D are graphs illustrating a heater, a control electrode, and states of bias in order to explain a pulse operating method for an FET-type sensor having a built-in heater according to the invention;

DETAILED DESCRIPTION OF THE INVENTION

In a pulse operating method for an FET-type sensor having a horizontal floating gate according to the invention, a pre-bias voltage pulse ($V_{pre}$) is applied to a control electrode to improve reactivity and recovery characteristics, and a voltage of the floating gate is changed depending on a change in work function and capacitance, so that a current flowing in source/drain is sensed. The reactivity and recovery time can be greatly reduced according to the magnitude of the pre-bias voltage pulse, and the current can be prevented from flowing in the source/drain in the pre-biasing period, so that it is possible to implement the pulse operating method with lower power.

Hereinafter, a pulse operating method for an FET-type sensor having a horizontal floating gate according to embodiments of the invention will be described in detail with reference to the accompanying drawings.

Figure 1A:
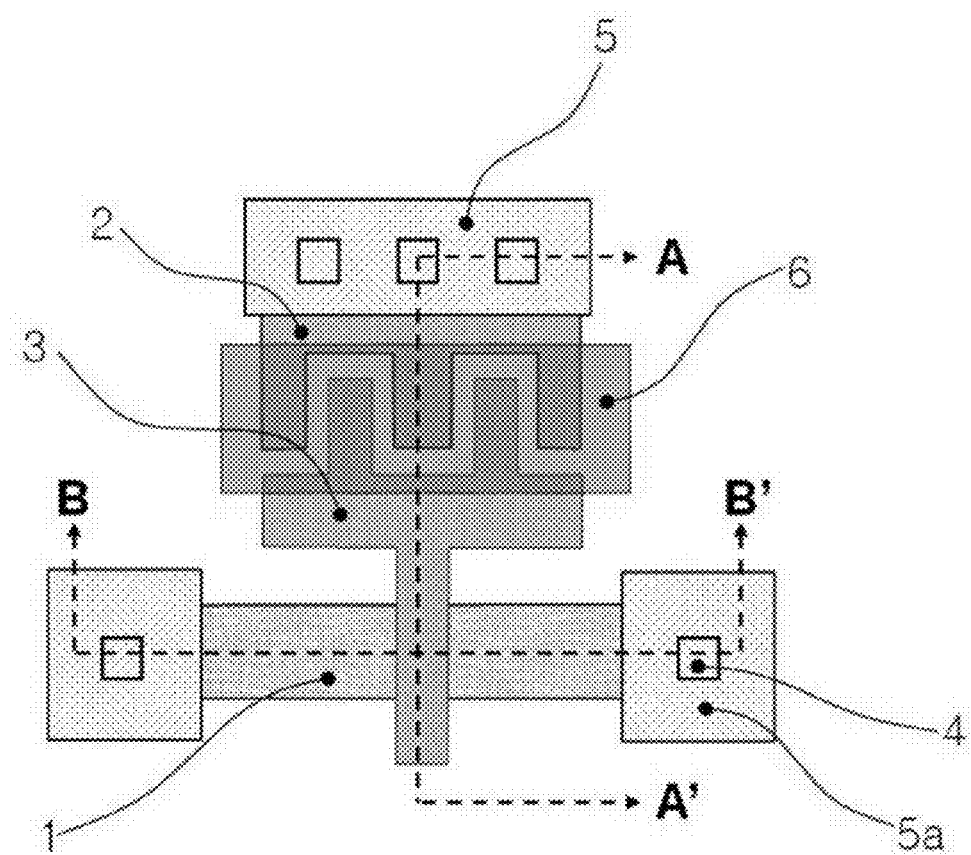
FIGS. 1A to 1D illustrate an FET-type sensor having a horizontal floating electrode capable of sensing a change in capacitance or generation/disappearance of charges.
Figure 2A:
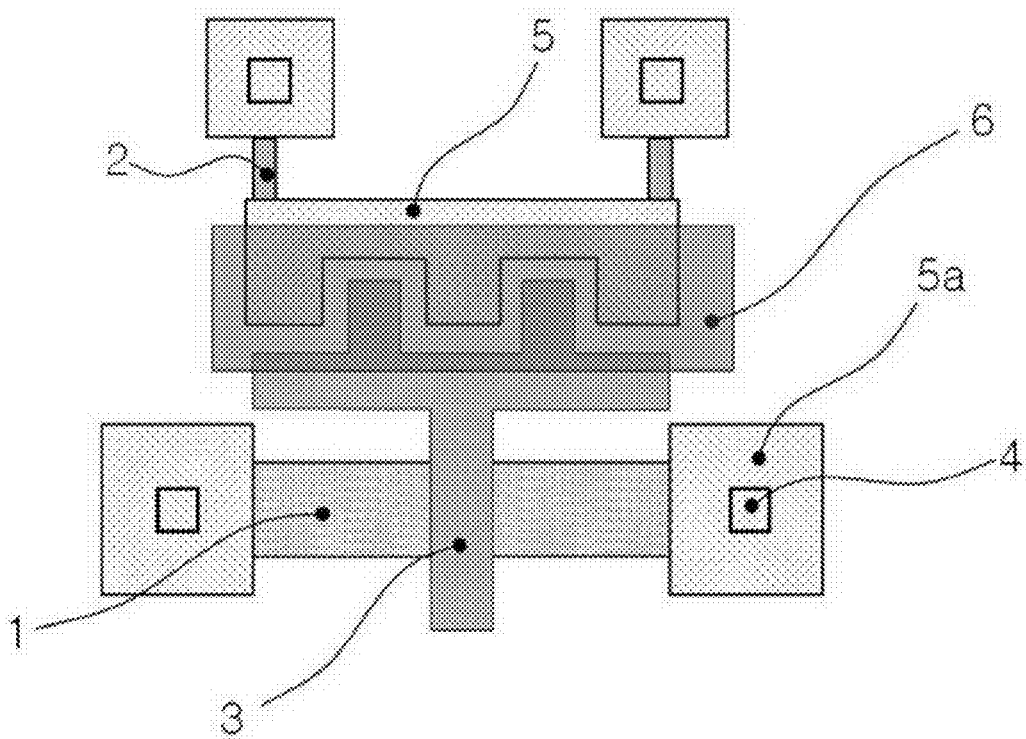
FIGS. 2A and 2B illustrate an FET-type sensor having a horizontal floating electrode capable of sensing a change in work function.

First, an FET-type sensor having a horizontal floating gate in the related art, to which the pulse operating method according to the invention can foe applied, will be described in brief. FIG. 1A and FIG. 2A are sensors that can sense a change in capacitance and work function as an example in the related art.

Figure 1B:
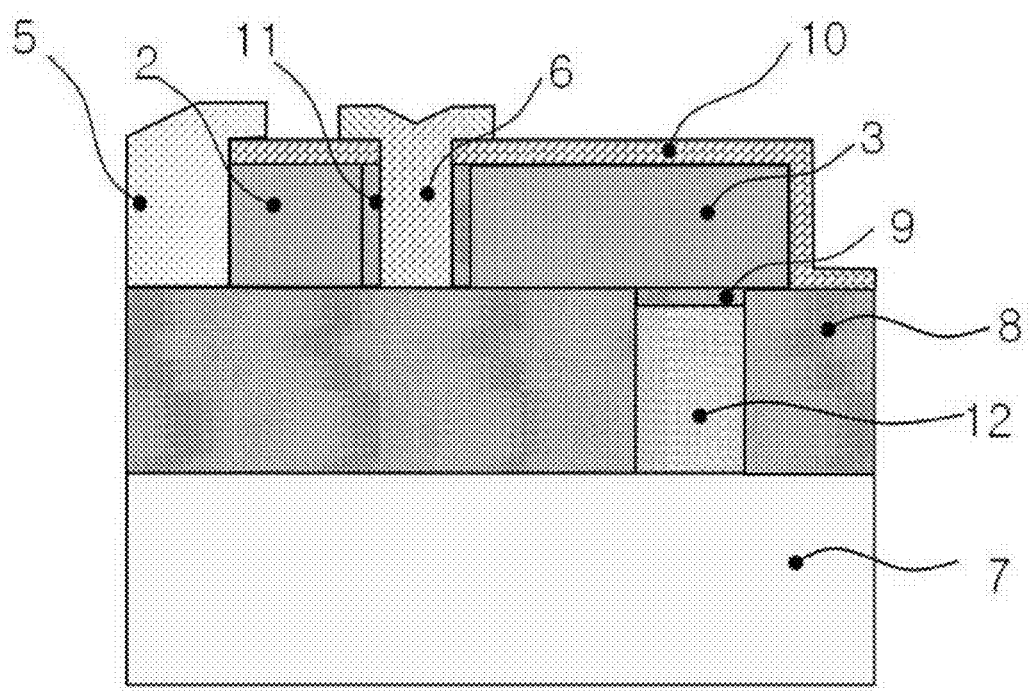

As illustrated in FIGS. 1A and 1B, a sensing material layer 6 is formed between a control electrode 2 and a floating electrode 3 facing each other with a protective insulating film interposed therebetween. A dielectric constant is changed during reaction, and thus, a coupling ratio is changed to directly affect a potential of the floating electrode 3, so that a voltage to be applied to the floating electrode 3 varies with an operating voltage applied to the control electrode 2 before and after the reaction. As a result, channel formation and/or channel resistance of a semiconductor body 12 are affected, and a gas is sensed with a current flowing through a source/drain electrode 5a.

Figure 1C:
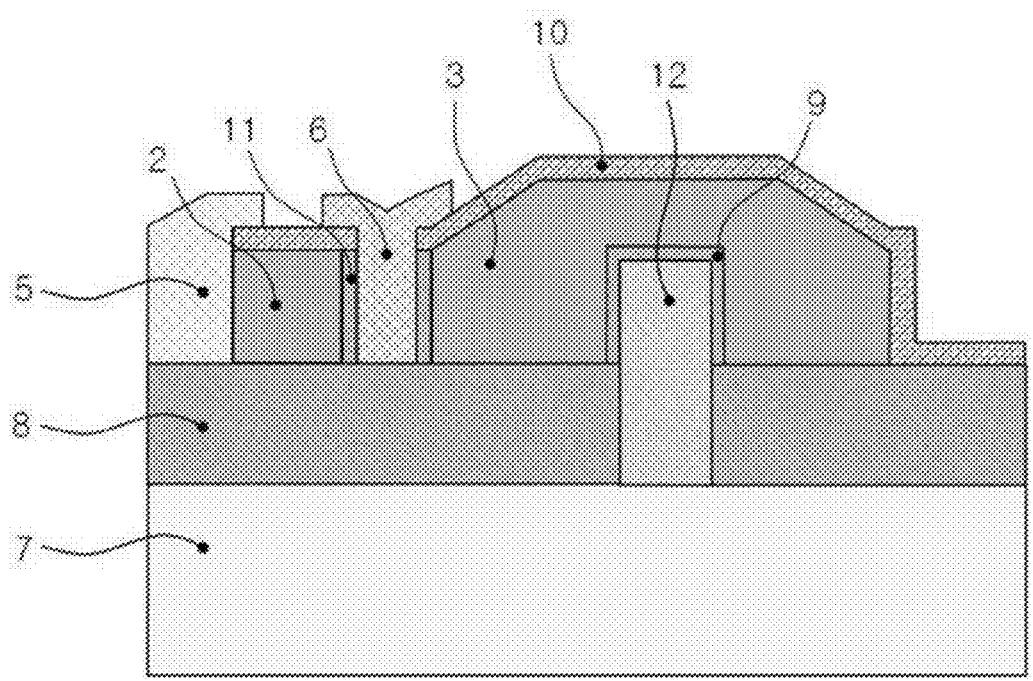
Figure 1D:
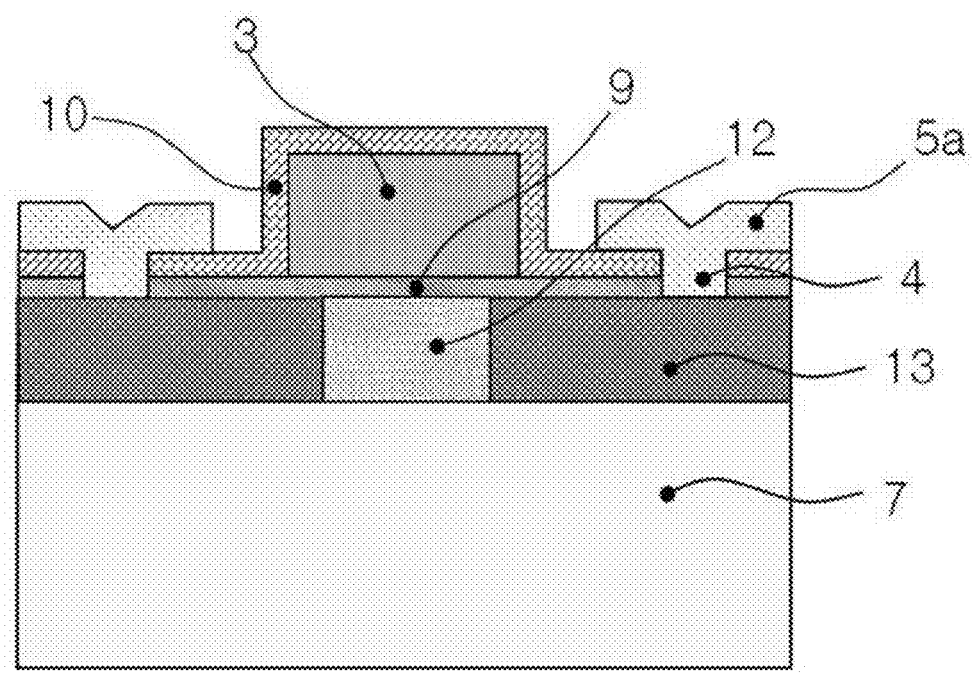

FIG. 1C is a structure of a three-dimensional Fin-FET-type sensor disclosed in Patent Document 2.

The three-dimensional Fin-FET-type sensor is configured to include: a semiconductor substrate; a semiconductor body formed to protrude from the semiconductor substrate; an isolation insulating film formed on a side surface of the semiconductor body and the semiconductor substrate; a gate insulating film formed on the semiconductor body; a floating electrode formed on the gate insulating film and the isolation insulating film; a control electrode formed on the isolation insulating film to face and be horizontally separated from at least one side surface of the floating electrode; a sensing material layer formed between the control electrode and the floating electrode; and source/drain regions formed in the semiconductor body with the floating electrode interposed therebetween, wherein the semiconductor body is formed on a lower side surface of the semiconductor body so that the semiconductor body protrudes, and wherein the floating electrode is formed to surround the semiconductor body protruding on the isolation insulating film with the gate insulating film interposed therebetween. The floating electrode is formed, so as to surround the semiconductor body protruding in the form of a fin, and thus, a channel width is enlarged, and a drain current is increased. Therefore, there is an advantage in that it is possible to increase the sensitivity of the sensor.

Figure 2B:
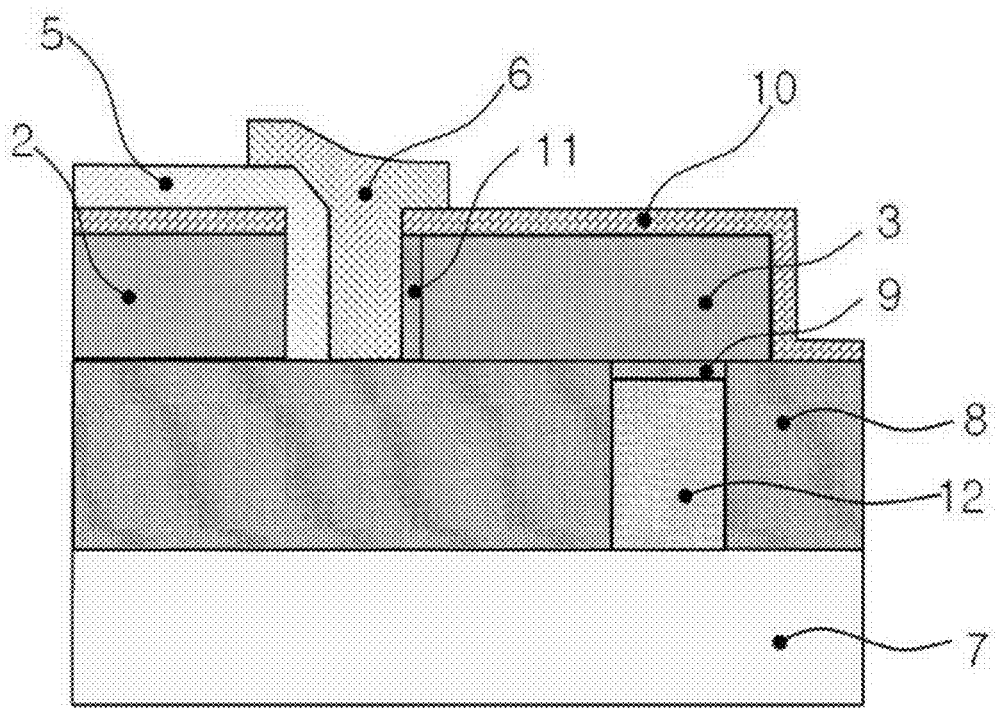

In the case where a first electrode 5 is formed between the control electrode 2 and the sensing material layer 6 as illustrated in FIGS. 2A and 2B, a change in electric potential between the floating electrode 2 and the floating electrode 3 according to a change in work function of the sensing material layer 6 is used as an operation mechanism. Namely, in the case where the sensing material layer 6 is made of a material that changes the work function due to reaction with a specific gas, since the sensing material layer 6 has a structure of being directly connected to the control electrode 2 through the first electrode 5, the work function of the control electrode 2 is changed. Even at the same operating voltage, the voltage to be transferred to the floating electrode 3 varies depending on the presence or absence of the specific gas, and this is sensed by a current flowing through the source/drain electrode 5a.

FIGS. 3A to 3F are graphs illustrating states of bias applied to electrodes in order to explain a pulse operating method for an FET-type sensor having a horizontal floating gate according to a first embodiment of the invention. The pulse operating method for an FET-type sensor having a horizontal floating gate according to the first embodiment of the invention includes a reading preparation step (pre-biasing step) and a reading step (read-biasing step). Herein, although the pre-biasing step may be omitted, it is preferable that the pre-biasing step is provided in terms of improvement of the reactivity and recovery characteristics.

In the above-described FET-type sensors having a horizontal floating gate, a voltage is applied in a form of a pulse to the control electrode and the drain electrode. A voltage ($V_{pre}$) for the pre-bias and a voltage ($V_{rCG}$) for the read-bias are applied to the control electrode with a combination of magnitudes, widths, order, and numbers of the pulses. Depending on the characteristics of the sensing gas, the pre-bias voltage pulse applied to the control electrode may be negative or positive. It is preferable that the voltage pulse applied to the drain electrode is synchronized with the read-bias voltage pulse applied to the control electrode.

When the pre-bias voltage pulse ($V_{pre}$) is applied to the control electrode, it is preferable that the voltage between the drain and the source is maintained at 0 V so that no current flows in the sensor.

At least one negative pre-bias voltage pulse, at least one read-bias voltage pulse, at least one positive pre-bias voltage pulse, and at least one read-bias voltage pulse are sequentially applied to the control electrode, or at least one positive pre-bias voltage pulse, at least one read-bias voltage pulse, at least one negative pre-bias voltage pulse, and at least one read-bias voltage pulse are sequentially applied to the control electrode, so that an oxidizing gas or a reducing gas can be determined.

Figure 3A:
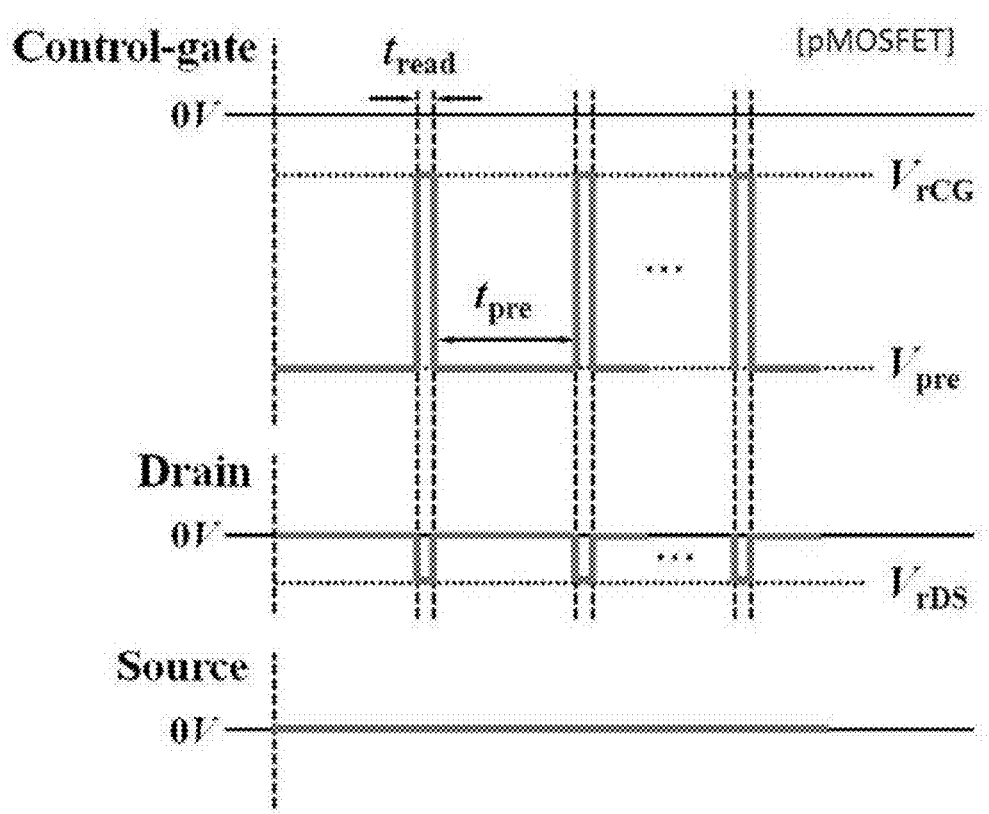
FIGS. 3A to 3E are graphs illustrating states of bias applied to a control electrode, a drain electrode, and a source electrode in order to explain a pulse operating method for an FET-type sensor according to the invention.
Figure 3B:
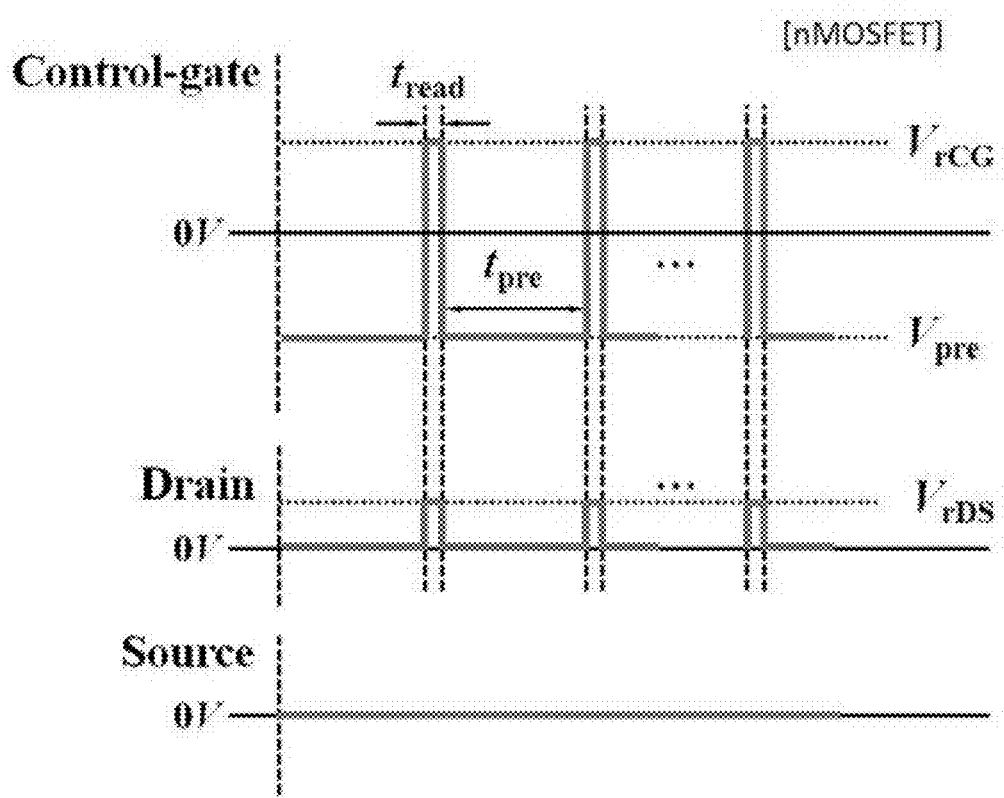
Figure 3C:
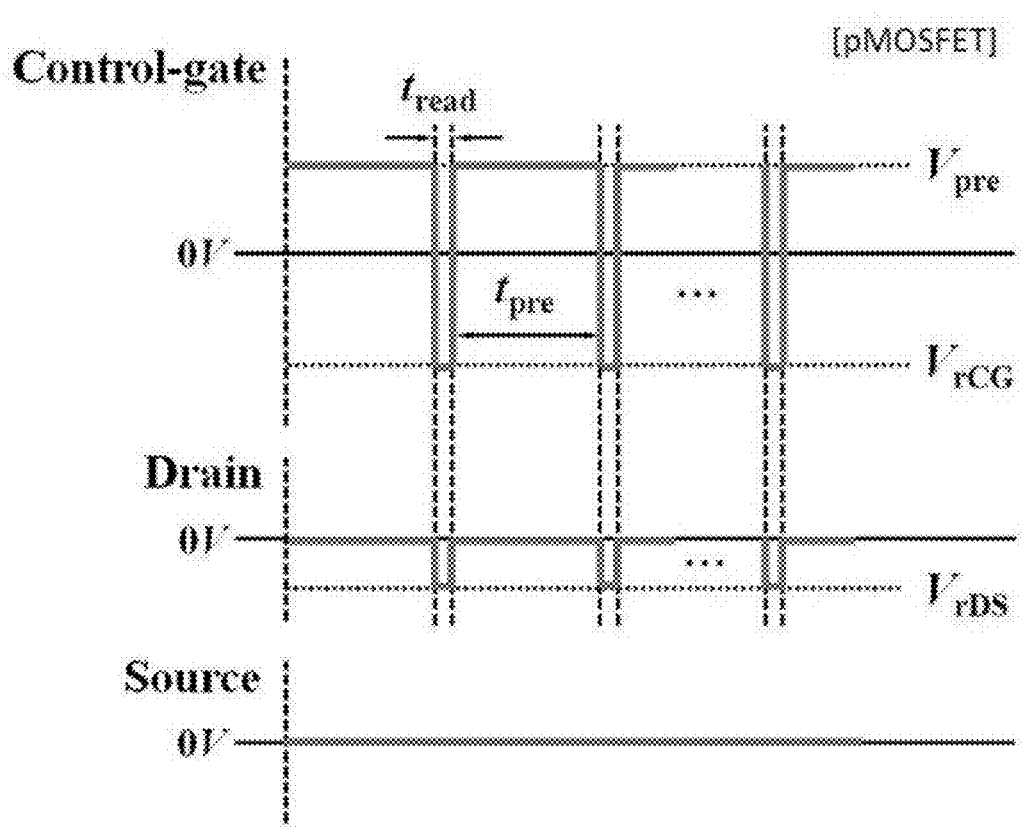
Figure 3D:
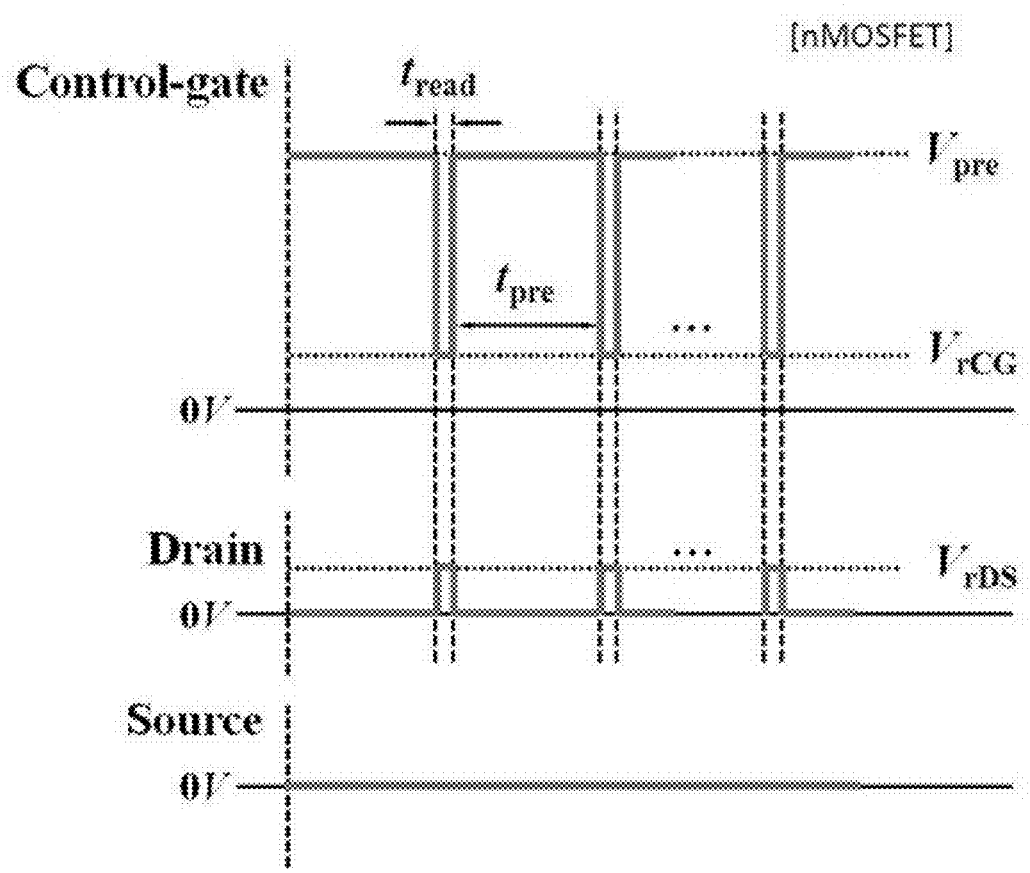
Figure 3E:
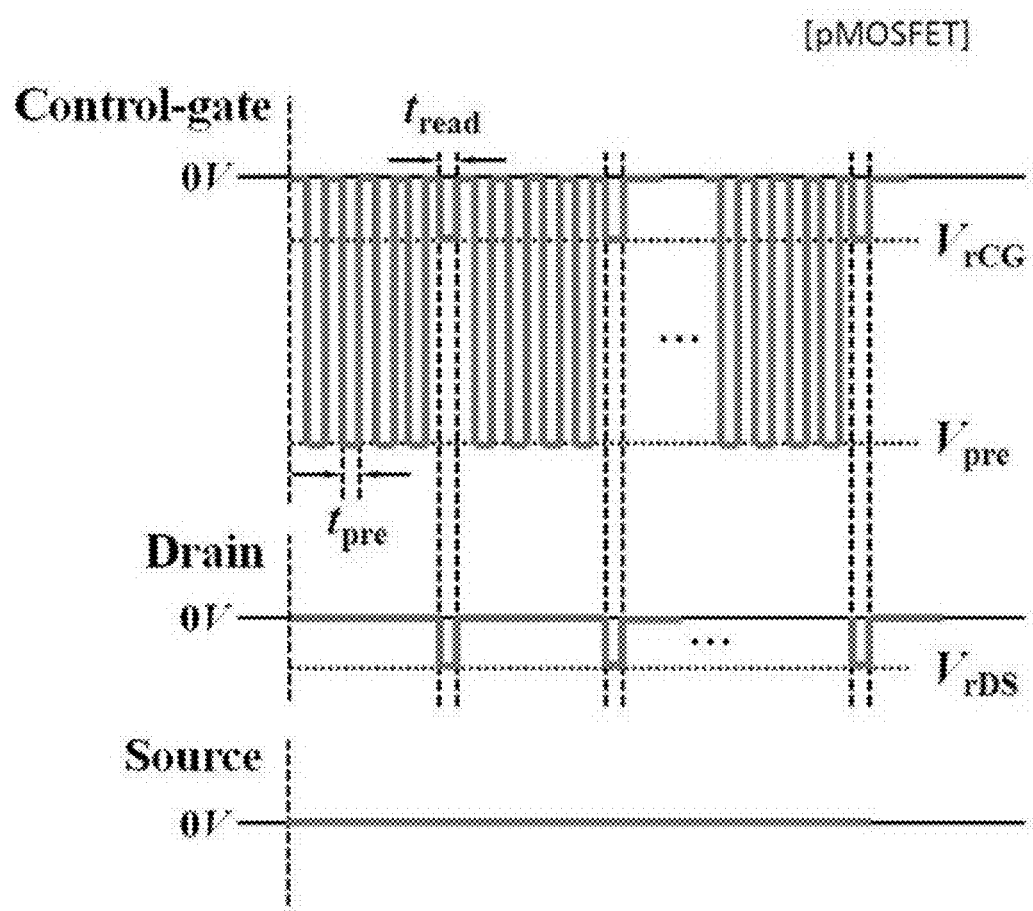

FIGS. 3A and 3B are graphs illustrating pulse operating methods for applying a negative pre-bias voltage pulse to the control electrodes of the p-MOSFET and the n-MOSFETtype sensor, respectively, and FIGS. 3C and 3D are graphs illustrating pulse operating methods for applying a positive pre-bias voltage pulse to the control electrodes of the p-MOSFET and the n-MOSFET-type sensor, respectively. FIG. 3E is a modified form of FIG. 3A and is a graph illustrating a pulse operating method where the number of pre-bias voltage pulses applied is different.

It is preferable that, in the case of the p-MOSFET, a negative read-bias voltage pulse is applied to the drain electrode, and in the case of the n-MOSFET, a positive read-bias voltage pulse is applied to the drain electrode.

Figure 4A:
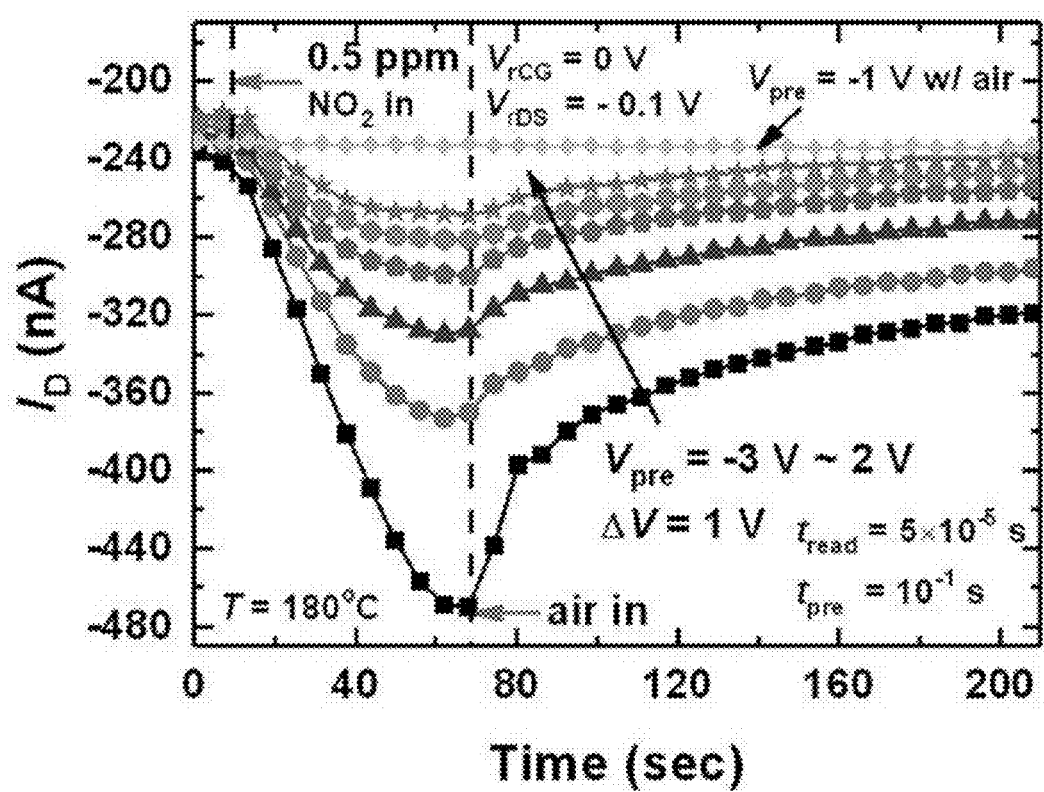
FIGS. 4A to 4C are graphs illustrating gas reactions measured in an FET-type sensor having a horizontal floating electrode as an example where the pulse operating method according to the invention is applied.
Figure 4B:
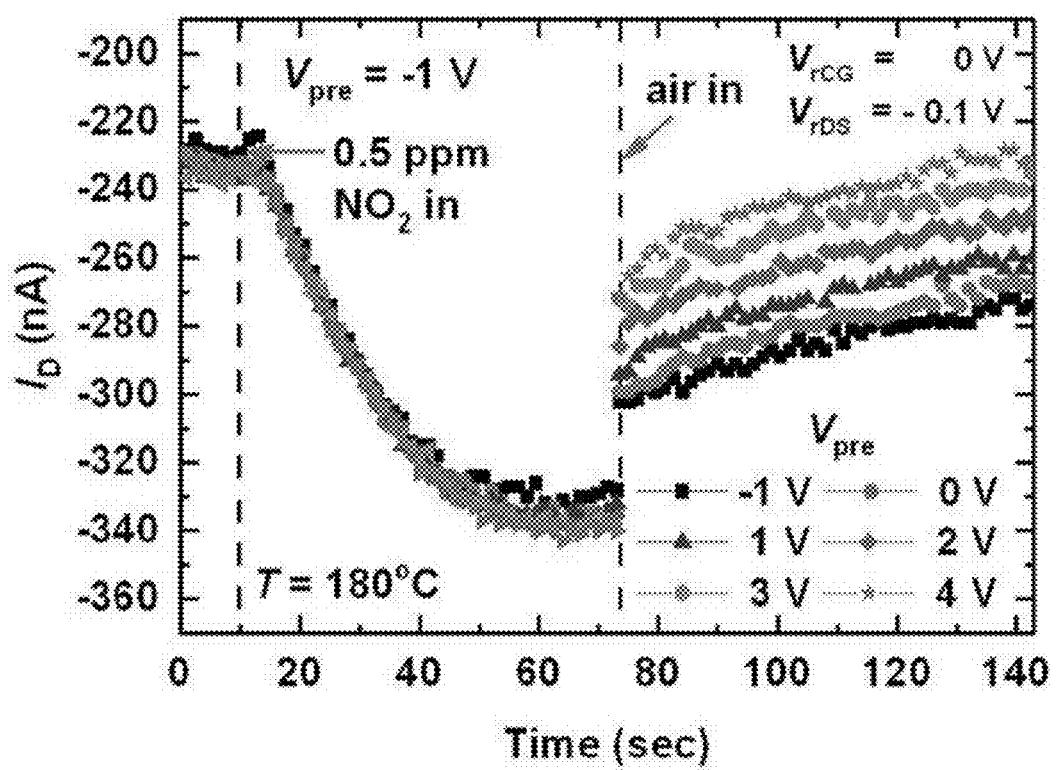
Figure 4C:
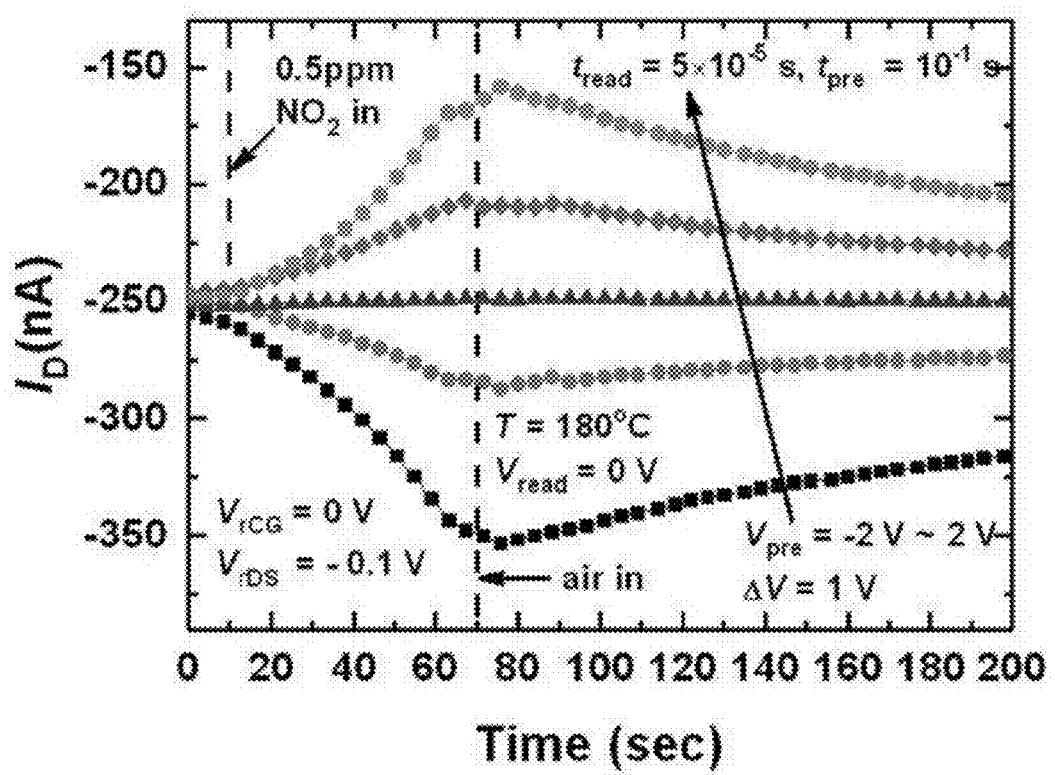

FIGS. 4A to 4C illustrate examples of application of the pulse operating method according to the first embodiment of the invention to a p-MOSFET-type gas sensor having ZnO as a sensing material and are graphs illustrating results of measurement of reactivity to nitrogen dioxide which is a typical oxidizing gas.

The pulse operating method is applied to a gas sensor, and a pre-bias voltage pulse is applied to the control electrode to adsorb or desorb a specific gas. In order to maximize the effect caused by the pre-bias voltage poise, it is preferable that a read-bias voltage pulse is applied to the control electrode immediately after the pre-bias voltage pulse is applied. In addition, it is preferable that power consumption is reduced by minimizing the width of the pulse.

FIG. 4A is an example of application of the pulse operating method for an FET-type gas sensor having a horizontal floating gate according to the first embodiment of the invention, which is also disclosed in Non-Patent Document 2. FIG. 4A illustrates a graph illustrating a result of measurement of reaction with nitrogen dioxide according to the magnitude of a negative pre-bias voltage pulse applied to a control electrode of a p-MOSFET-type gas sensor having a change in work function as a sensing mechanism disclosed in Patent Document 1.

As illustrated in FIG. 2A, in the FET-type gas sensor having a change in work function as a sensing mechanism, the control electrode and the sensing material layer are electrically connected to each other, and thus, the concentration of electrons at the interface between the sensing material layer 6 and the protective insulating film 10 surrounding the floating electrode 3 is Changed according to an applied pre-bias voltage pulse. When a negative pre-bias voltage pulse is applied, the energy band of the sensing material layer electrically connected to the control electrode is raised, so that electrons are accumulated at the interface between the sensing material layer 6 and the protective insulating film 10 surrounding the floating electrode 3. In the sensing material layer near the interface, the nitrogen dioxide is ionized by the electrons, and the adsorption reaction actively occurs in the sensing material layer.

Thus, the concentration of electrons in the sensing material layer is lowered, so that the work function is increased. Therefore, as illustrated in FIG. 4A, the magnitude of the current flowing in the source/drain of the p-MOSFET is increased. In addition, as the magnitude of the negative pre-bias voltage pulse applied to the control electrode is increased, the concentration of electrons accumulated at the interface between the sensing material layer and the protective insulating film 10 surrounding the floating electrode 3 is increased, and thus, the number of the reacting nitrogen dioxide is increased. Therefore, the work function is increased, so that the reactivity is increased.

FIG. 48 illustrates an example of application of the pulse operating method according to the invention and is a graph illustrating a result of measurement of recovery time improved by allowing a p-MOSFET-type gas sensor having a change in work function as a sensing mechanism disclosed in Patent Document 1 to react with nitrogen dioxide and, after that, applying a positive pre-bias voltage pulse to the control electrode. As illustrated in FIG. 4B, in the period from 10 to 70 seconds, a negative pre-bias voltage pulse is applied to the control electrode in the state where nitrogen, dioxide is injected, and in the period from 70 to 140 seconds, in order to check gas recovery characteristics, a degree of recovery according to the pre-bias voltage pulse is measured while injecting air.

When a positive pre-bias voltage pulse is applied to the control electrode, the energy band of the sensing material layer 6 electrically connected to the control electrode is lowered, and thus, the electron depletion region is formed at the interface between the sensing material layer and the protective insulating film 10. Thus, electrons can easily migrate from the ionized nitrogen dioxide to the sensing material layer, so that the work function of the sensing material layer is decreased. Therefore, the magnitude of the current flowing in the source/drain of the p-MOSFET is decreased.

In addition, as illustrated in FIG. 4B, as the magnitude of the pre-bias voltage pulse applied to the control electrode is increased, the electron depletion layer caused by the pre-bias is increased at the interface of the sensing material layer and the protective insulating film 10 surrounding the floating electrode 3, the nitrogen dioxide loses electrons and is desorbed, and thus, the recovery characteristics is improved.

FIG. 4C is a graph illustrating a gas reaction in the case where the pulse operating method according to the first embodiment of the invention is applied to the FET-type gas sensor of FIGS. 1A to 1D. As illustrated in FIG. 1B, the sensing material layer 6 fills on and between the control electrode 2 and the floating electrode 3 covered with the protective insulating film 10. Therefore, when a positive voltage is applied to the control electrode, electrons are accumulated in the sensing material layer formed on the first insulating film 11 covering the control electrode, and electrons are depleted in the sensing material layer formed on the first insulating film covering the floating electrode. On the other hand, when a negative voltage is applied to the control electrode, electrons in the sensing material layer formed on the first insulating film covering the control electrode are depleted, and electrons are accumulated in the sensing material layer formed on the first insulating film covering the floating electrode.

When a positive pre-bias voltage pulse is applied to the control electrode, electrons are depleted in a portion of the sensing material layer closer to the floating electrode, but electrons are accumulated in a portion of the sensing material layer closer to the control electrode, so that the ionization reaction of nitrogen dioxide actively occurs. Electrons are depleted by the nitrogen dioxide adsorbed in the portion of the sensing material layer closer to the control electrode, and thus, the capacitance is reduced. Therefore, the coupling ratio is decreased, and the magnitude of the voltage transferred to the floating electrode is reduced, so that the magnitude of the source/drain current of the p-MOSFET is decreased.

On the other hand, when a negative pre-bias voltage pulse is applied to the control electrode, electrons are depleted in the portion of the sensing material layer closer to the control electrode, but electrons are accumulated in the portion of the sensing material layer closer to the floating electrode, so that the ionization reaction of nitrogen dioxide actively occurs. Electrons are depleted by the nitrogen dioxide adsorbed in the portion of the sensing material layer closer to the floating electrode. Therefore, the work function is increased, so that the magnitude of the source/drain current of the p-MOSFET is increased.

Accordingly, by applying the pulse operating method according to the first embodiment of the invention and using the s sensing material and gas sensor, it is possible to improve the reactivity and the recovery characteristics, the influence of the pre-biasing is different depending on a structure of the FET-type gas sensor, and since a current flows in the source/drain only in the read-biasing period, the FET-type gas sensor can operate with low power.

In order to explain a pulse operating method for an FET-type gas sensor having a horizontal floating gate with a built-in heater according to a second embodiment of the invention, a structure of an FET-type gas sensor having a heater disclosed in Patent Document 1 in the related art will be described in brief.

Figure 5A:
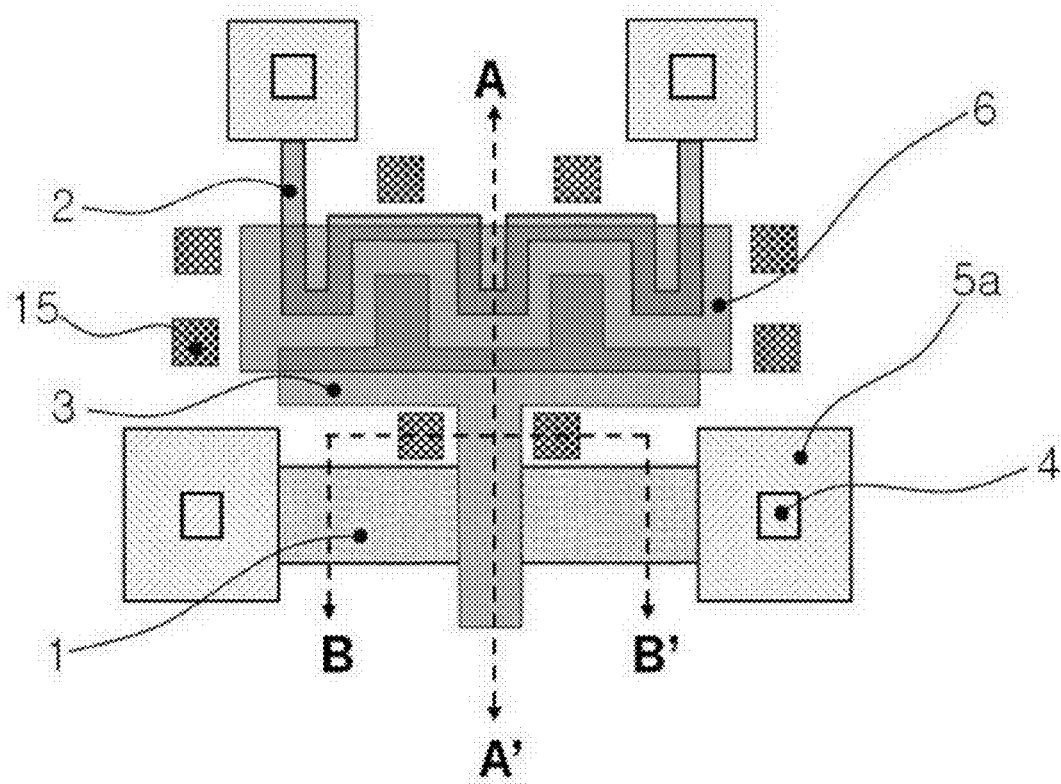
FIG. 5A is a plan view of an FET-type sensor having a built-in heater.
Figure 5B:
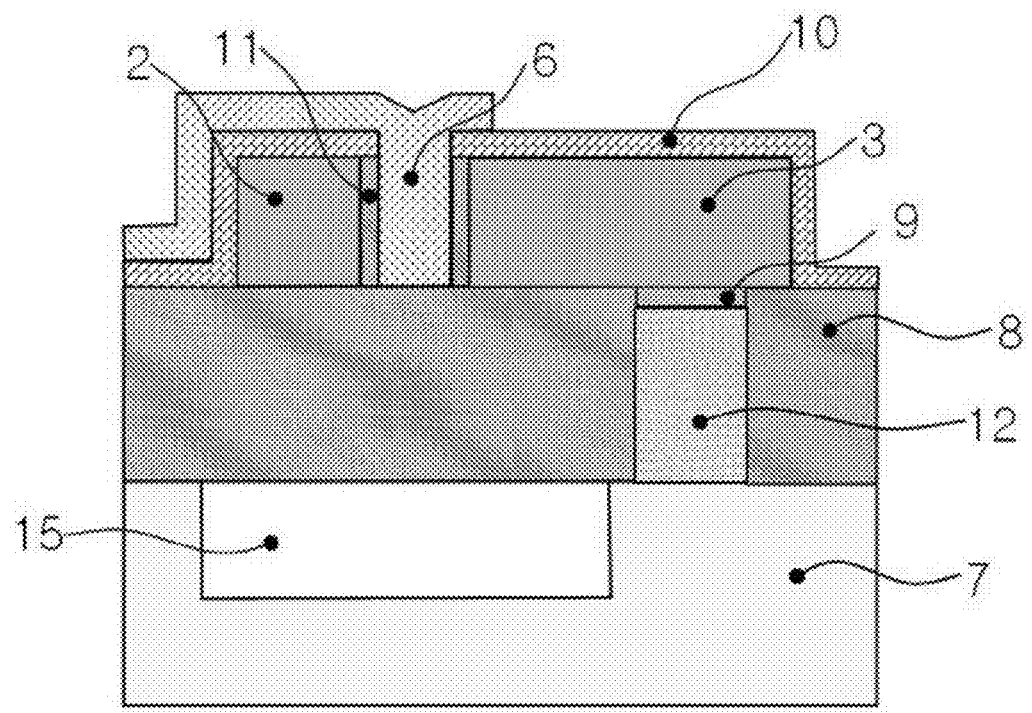
FIG. 5B is a cross-sectional view taken along line A-A' in FIG. 5A.
Figure 5C:
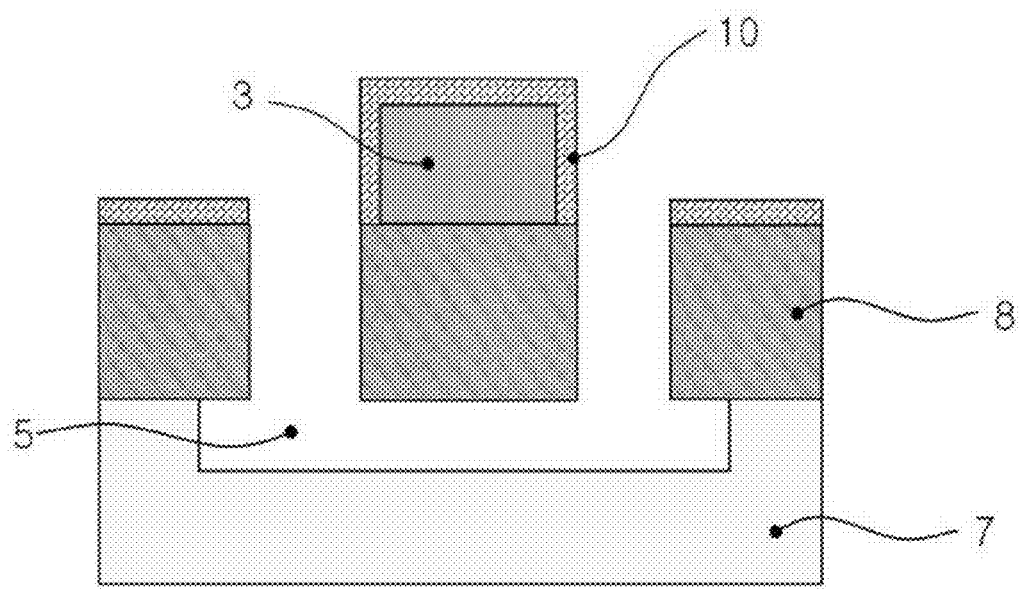
FIG. 5C is a cross-sectional view taken along line B-B' in FIG. 5A.
Figure 6A:
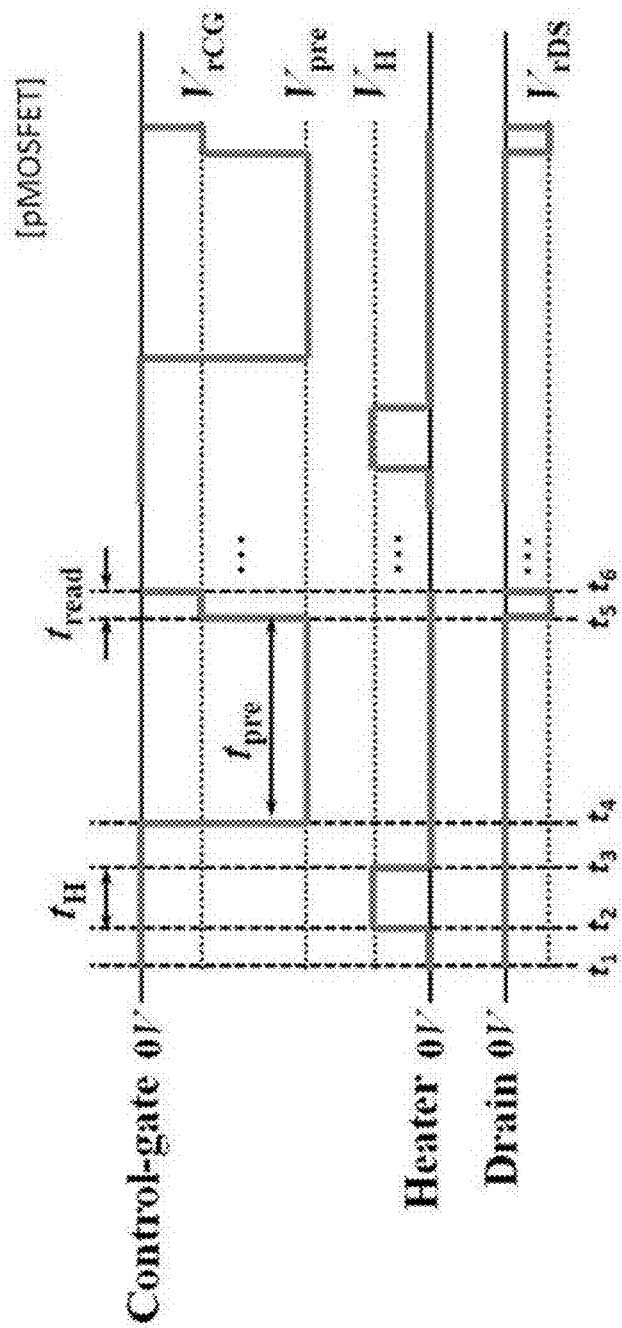
Figure 6C:
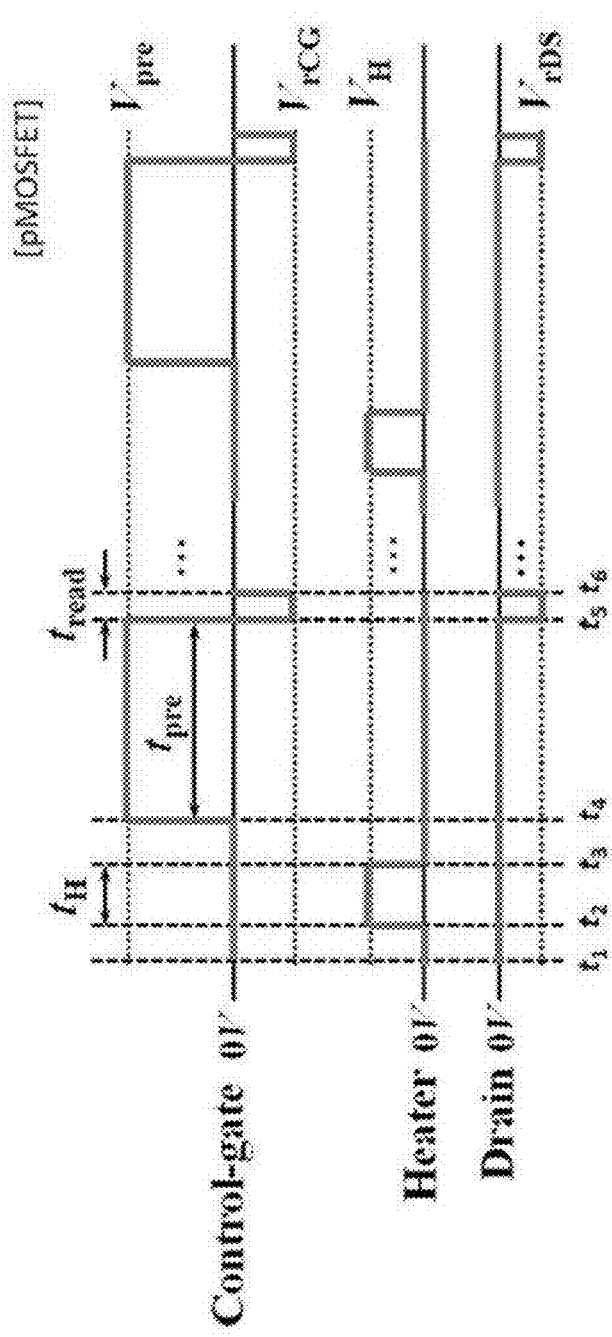
Figure 6D:
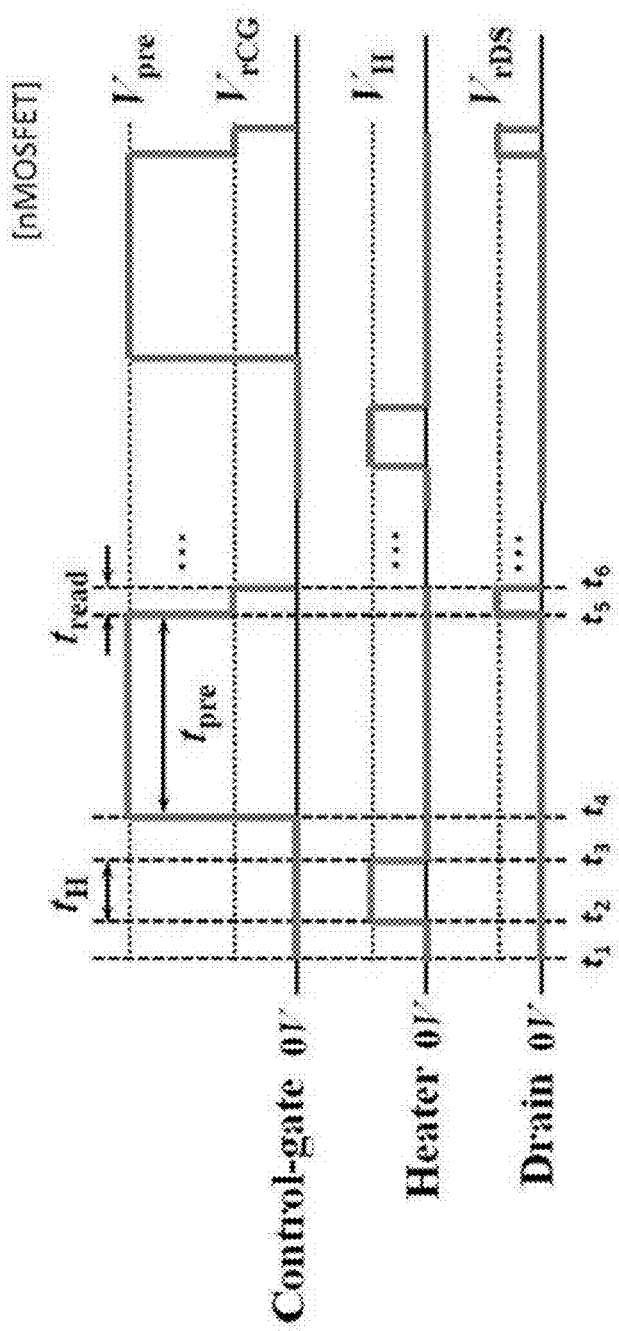

FIGS. 5A to 5C are diagrams illustrating a structure of an FET-type sensor having a horizontal floating gate with a built-in heater in the related art. By applying a voltage to both ends of the control electrode the FET-type sensor can be used as a heater. There is an advantage in that, by applying a voltage to the control electrode 2, a current flows to generate heat, and thus, reactivity can be improved.

As illustrated in FIGS. 5B to 5C, the semiconductor substrate 7 under the control electrode 2 and the sensing material layer 6 are etched to a predetermined depth to form an air layer 15.

As described above, there is an advantage in that, by forming the air layer 15 below the control electrode 2 and the sensing material layer 6, the heat generated in the control electrode 2, which acts as a heater, is transferred to the semiconductor substrate 7 having high thermal conductivity, so that it can be effectively transfer the heat to the sensing material layer 6.

Besides the structures illustrated in FIGS. 5A to 5C, a structure of the FET-type sensor having a built-in heater may be used where a control electrode is formed with a specific length on an isolation insulating film to be horizontally separated from at least one side surface of a floating electrode 3 on which a protective insulating film is formed, and the control electrode can be used as a heater. In addition, after a floating electrode 3 is formed, a control electrode maybe formed with a specific length on an isolation insulating film to be horizontally separated from at least one side surface of the floating electrode, and a protective insulating film may be formed thereon.

In addition, a structure may be used where a control electrode is formed on an isolation insulating film and a heater electrode covered with a protective insulating film.

A pulse operating method of a sensor having a horizontal floating gate with a built-in heater according to a second embodiment of the invention will be described in detail with reference to FIGS. 6A to 6D.

FIGS. 6A to 6D are graphs illustrating states of bias applied to electrodes in order to explain the pulse operating method for an FET-type sensor having a horizontal floating gate with a built-in heater according to the embodiment of the invention. The pulse operating method for an FET-type sensor having a horizontal floating gate with a built-in heater according to the first embodiment of the invention includes a heating step, a pre-biasing step, and a reading step.

Similarly to the first embodiment of the invention, in order to improve the reactivity and recovery characteristics of the control electrode of the FET-type sensor having a horizontal floating gate with a built-in heater, a voltage for heating, a pre-bias voltage pulse, and a voltage for read-bias are applied in combination of magnitudes, widths, order, and numbers of the pulses.

As illustrated in FIGS. 6A to 6D the heat-bias voltage pulse, the pre-bias voltage pulse, and the read-bias voltage pulse are applied to the control electrode in combination of the pulses. The voltage for heating is applied to the control electrode to heat the sensitive material layer 6 in the period from t2 to t3, the pre-bias voltage pulse is applied to the control electrode to start reaction in the period from t4 to t5, and the read-bias voltage pulse is applied to the control electrode and the drain electrode to sense a gas with a change in source/drain current caused by the reaction. At t1 to t2 and t3 to t4, a voltage of 0 V can be applied to all the electrodes to reduce power consumption, and the heat-bias, pre-bias, and read-bias voltage pulses can be applied in combination of magnitudes, widths, order, and numbers of the pulses.

At least one heat-bias voltage pulse is applied prior to the pre-bias voltage pulse and the read-bias voltage pulse, and the read-bias voltage pulse is applied after the heat-bias voltage pulse. Alternatively, the heat-bias voltage pulse, the pre-bias voltage pulse, and the read-bias voltage pulse are applied in this order.

At least one heat-bias voltage pulse is applied prior to the pre-bias and read-bias voltage pulses. At least one negative pre-bias voltage pulse, at least one read-bias voltage pulse, at least one positive pre-bias voltage pulse, and at least one read-bias voltage pulse are sequentially applied to the control electrode, or at least one positive pre-bias voltage pulse, at least one read-bias voltage pulse, at least one negative pre-bias voltage pulse, and at least one read-bias voltage pulse are sequentially applied to the control electrode, so that an oxidizing gas and a reducing gas can be distinguished from each other.

It is preferable that the read-bias voltage pulse applied to the drain electrode is synchronized with the read-bias voltage pulse applied to the control electrode, and the voltage between the drain and the source is maintained at 0 V in the remaining period so that no current flows in the source and the drain. Since the heat-bias voltage pulse, the pre-bias voltage pulse, and the read-bias voltage pulse are applied in a pulse form, it is possible to allow the FET-type sensor to operate with lower power in comparison with a DC operating method.

A third embodiment of the invention is a pulse operating method of a sensor array including a plurality of sensors operating as sensing mechanisms.

A pre-bias voltage pulse and a read-bias voltage pulse are applied to a plurality of the control electrodes in combination of magnitudes, widths, order, and numbers of the pulses. In addition, negative or positive pre-bias voltage pulses may be applied to a plurality of the control electrodes in synchronization with each other, or the pulses may be applied differently to the respective control electrodes.

The voltage pulses may be applied to a plurality of the drain electrodes in synchronization with each other to perform a read operation at a time, or the voltage pulses can be applied to a plurality of the drain electrodes in an order, and the voltage applied to all the sources is maintained at 0 V.

Figure 7:
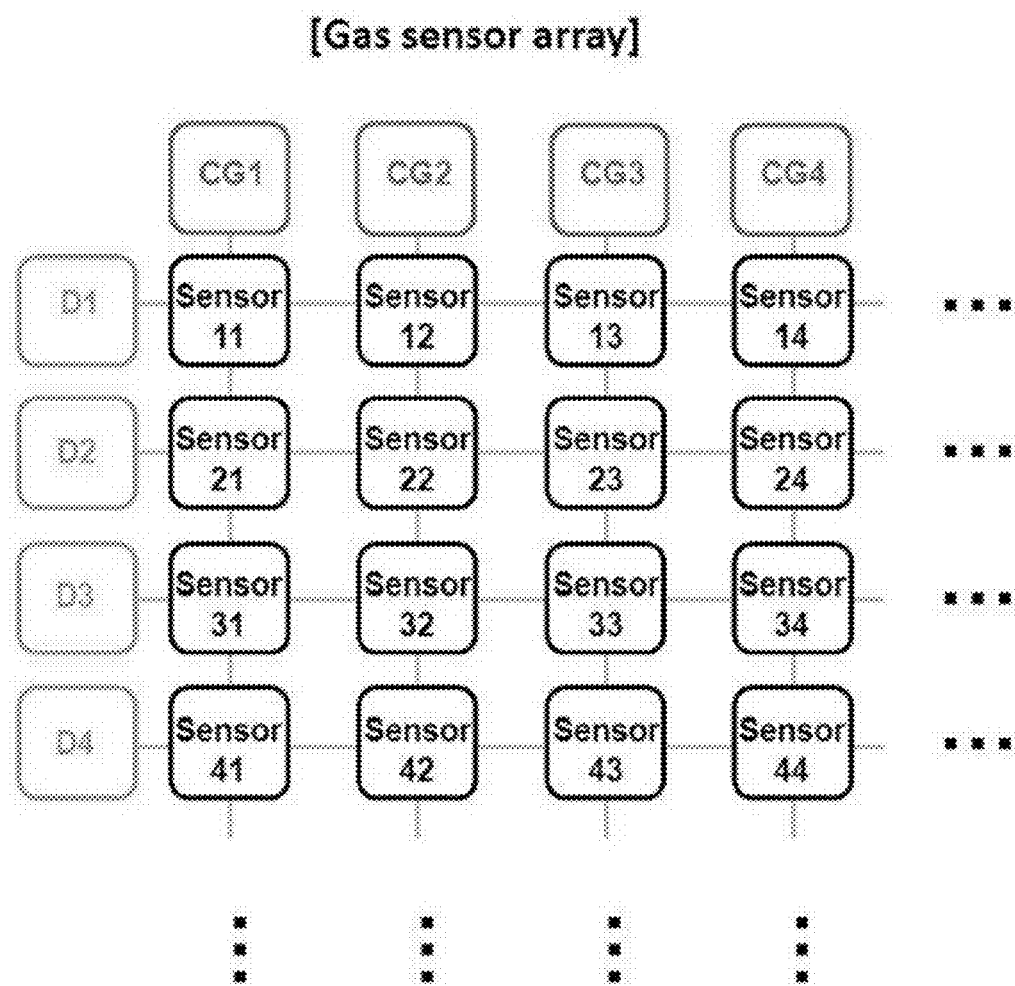
FIG. 7 illustrates an example where a plurality of sensors according to the invention are arranged to constitute a sensor array.
Figure 8:
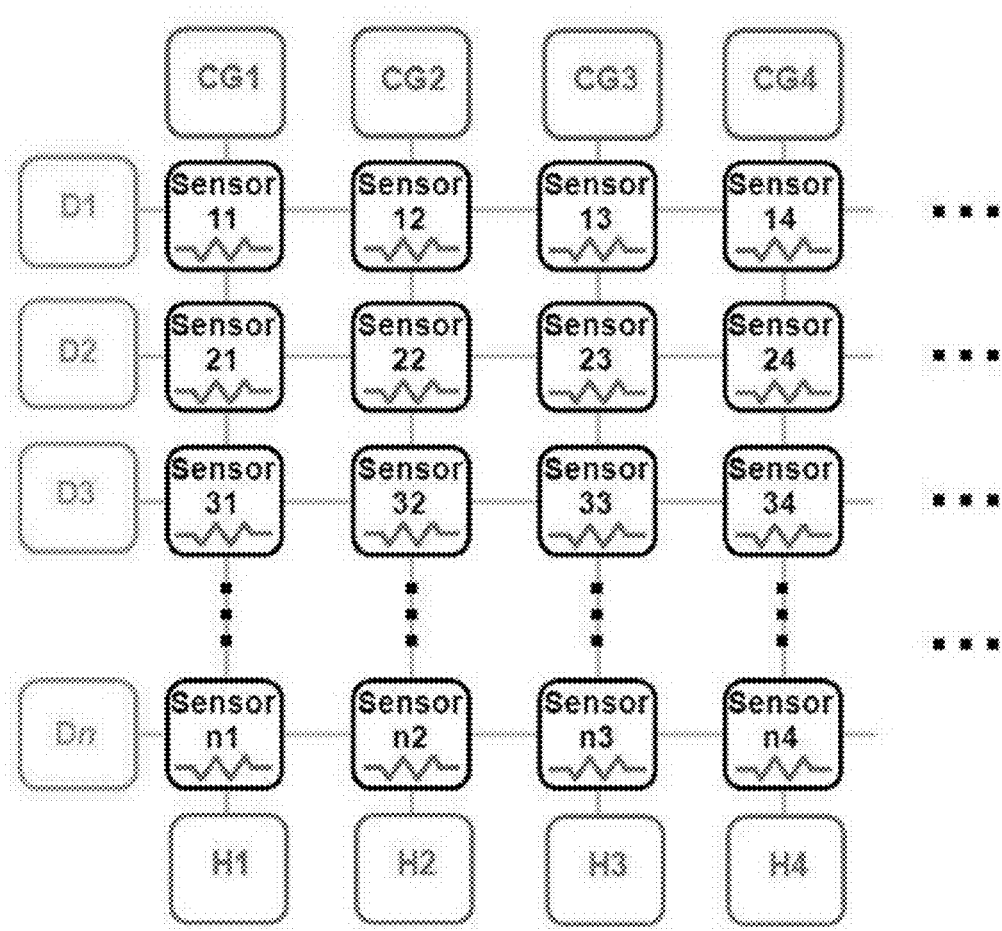
FIG. 8 illustrates an example where a plurality of sensors having a built-in heater according to the invention are arranged to constitute a sensor array.

FIG. 7 illustrates a sensor array including FET-types sensors (referred to as sensing means) having different sensing mechanisms where sensing material layers are different or structures of the FET-type sensors are different.

According to the third embodiment of the invention, by applying the pulses to the drain electrode and the control electrode, it is possible to improve the reactivity and recovery characteristics in the sensor array.

In a fourth, embodiment of the invention, the pulse operating method according to the first embodiment is applied to a sensor array where two or more FET-type sensors having different sensing mechanisms due to different cross-sectional structures with a built-in heater or different, sensing materials are formed in one semiconductor substrate.

FIG. 3 illustrates an FET-type gas sensor array with a built-in heater. The heat-bias voltage pulse, the pre-bias voltage pulse, and the read-bias voltage pulse according to the second embodiment of the invention are applied to the control electrode, so that it is possible to improve the gas reactivity and recovery characteristics in the sensor array and to allow the sensor array to operate with low power.

For example, when the above-described pulse operating method is applied to a gas sensor array, since an operating temperature is different depending on a sensing material layer, a heater operating voltage suitable for specific gas sensing characteristics can be applied. Similarly to the third embodiment of the invention, all the same or different pre-bias voltages can be applied to the control electrodes of the sensor array, and all the same or different voltages can be applied to the drain electrodes.

While the present invention has been particularly illustrated and described with reference to exemplary embodiments thereof, it should be understood by the skilled in the art that the invention is not limited to the disclosed embodiments, but various modifications and applications not illustrated in the above description can be made without departing from the spirit of the invention. In addition, differences relating to the modifications and applications should be construed as being included within the scope of the invention as set forth in the appended claims.

What is claimed is:

1. A pulse operating method for an FET-type sensor including a semiconductor body formed to protrude from a semiconductor substrate, a gate insulating film formed on the semiconductor body, a floating electrode formed on the gate insulating film, a control electrode formed to face and be horizontally separated from at least one side surface of the floating electrode, a sensing material layer positioned on the control electrode and at least horizontally opposite sidewall of the floating electrode, and a source and a drain formed in the semiconductor body with the floating electrode interposed therebetween, the pulse operating method comprising:
   a reading preparation step of applying one or more pre-bias voltage pulses ($V_{pre}$) as read preparation voltage pulses to the control electrode; and
   a reading step of applying one or more read-bias voltage pulses ($V_{rCG}$) as read voltage pulses to the control electrode and applying a voltage pulse ($V_{rDS}$) synchronized with the read voltage pulse between the drain and the source,
   wherein the pre-bias and read-bias voltage pulses are applied in combination of magnitudes, widths, order, and numbers of the pulses.

2. The pulse operating method according to claim 1, wherein the reading preparation step and the reading step are alternately performed, and
   wherein, while the pre-bias voltage pulse is applied in the reading preparation step, a voltage between the source and the drain is maintained at 0 V.

3. The pulse operating method according to claim 1, wherein the reading preparation step and the reading step are alternately performed,
   wherein one or more negative pre-bias voltage pulses are applied to the control electrode in the first reading preparation step of the reading preparation steps, and one or more positive pre-bias voltage pulses are applied to the control electrode in the second reading preparation step, or
   one or more positive pre-bias voltage pulses are applied to the control electrode in the first reading preparation step of the reading preparation steps, and one or more negative pre-bias voltage pulses are applied to the control electrode in the second reading preparation step, and
   wherein, while the pre-bias voltage pulse is applied in the reading preparation steps, a voltage between the source and the drain is maintained at 0 V.

4. The pulse operating method according to claim 1, wherein, in the case of sensing an oxidizing gas, the reading preparation step of applying a negative pre-bias voltage pulse and the reading step of applying a read-bias voltage pulse are sequentially performed,
   wherein, in the case of sensing an reducing gas, the reading preparation step of applying a positive pre-bias voltage pulse and the reading step of applying a read-bias voltage pulse are sequentially performed, and
   wherein, while the pre-bias voltage pulse is applied in the reading preparation step, a voltage between the source and the drain is maintained at 0 V.

5. The pulse operating method according to claim 1, wherein the control electrode of the FET-type sensor is configured to have a predetermined length so as to be used as a heater electrode,
   wherein the pulse operating method further comprises a heating step of applying one or more heat-bias voltage pulses to the control electrode, and
   wherein the heat-bias voltage pulses are applied in combination of magnitudes, widths, order, and numbers of the heat-bias voltage pulses.

6. The pulse operating method according to claim 5, wherein the heating step is performed before the reading preparation step and the reading step, and the reading preparation step and the reading step are alternately performed, and
   wherein, in the heating step and the reading preparation step, a voltage between the drain and the source is maintained at 0 V.

7. The pulse operating method according to claim 5, wherein the heating step is performed before the reading preparation step and the reading step,
   wherein the reading preparation step and the reading step are alternately performed,
   wherein one or more negative pre-bias voltage pulses are applied to the control electrode in the first reading preparation step of the reading preparation steps, and one or more positive pre-bias voltage pulses are applied to the control electrode in the second reading preparation step, or
   one or more positive pre-bias voltage pulses are applied to the control electrode in the first reading preparation step of the reading preparation steps, and one or more negative pre-bias voltage pulses are applied to the control electrode in the second reading preparation step, and
   wherein, in the heating step and the reading preparation step, a voltage between the drain and the source is maintained at 0 V.

8. The pulse operating method according to claim 5,
wherein the heating step is performed before the reading preparation step and the reading step,
wherein, in the case of sensing an oxidizing gas, the reading preparation step of applying a negative pre-bias voltage pulse and the reading step of applying a read-bias voltage pulse are sequentially performed,
wherein, in the case of sensing a reducing gas, the reading preparation step of applying a positive pre-bias voltage pulse and the reading step of applying a read-bias voltage pulse are sequentially performed, and
wherein, in the heating step and the reading preparation step, a voltage between the drain and the source is maintained at 0 V.

9. The pulse operating method according to claim 5,
wherein a step of sequentially performing the reading step and the heating step is repeated once or more times, and
wherein, in the heating step, a voltage between the drain and the source is maintained at 0 V.

10. The pulse operating method according to claim 5,
wherein the heating step is performed before the reading preparation step and the reading step,
wherein the heating step and the reading step are sequentially performed, or the heating step, the reading preparation step, and the reading step are sequentially performed, and
wherein, in the heating step and the reading preparation step, a voltage between the drain and the source is maintained at 0 V.

11. The pulse operating method according to claim 10, wherein a step of sequentially performing the heating step and the reading step or a step of sequentially performing the heating step, the reading preparation step, and the reading step are repeated twice or more times.

12. The pulse operating method according to claim 1,
wherein the FET-type sensor further includes a heater electrode having a predetermined length which is formed to face and be horizontally separated from at least one side surface of the floating electrode,
wherein the pulse operating method further comprises a heating step of applying one or more heat-bias voltage pulses to the heater electrode, and
wherein the heat-bias voltage pulses are applied in combination of magnitudes, widths, order, and numbers of the heat-bias voltage pulses.

13. The pulse operating method according to claim 12,
wherein the heating step is performed before the reading preparation step and the reading step,
wherein the reading preparation step and the reading step are alternately performed, and
wherein, in the heating step and the reading preparation step, a voltage between the drain and the source is maintained at 0 V.

14. The pulse operating method according to claim 12,
wherein the heating step is performed before the reading preparation step and the reading step,
wherein the reading preparation step and the reading step are alternately performed,
wherein one or more negative pre-bias voltage pulses are applied to the control electrode in the first reading preparation step of the reading preparation steps, and one or more positive pre-bias voltage pulses are applied to the control electrode in the second reading preparation step, or
one or more positive pre-bias voltage pulses are applied to the control electrode in the first reading preparation step of the reading preparation steps, and one or more negative pre-bias voltage pulses are applied to the control electrode in the second reading preparation step, and
wherein, in the heating step and the reading preparation step, a voltage between the drain and the source is maintained at 0 V.

15. The pulse operating method according to claim 12,
wherein the heating step is performed before the reading preparation step and the reading step,
wherein, in the case of sensing an oxidizing gas, the reading preparation step of applying a negative pre-bias voltage pulse and the reading step of applying a read-bias voltage pulse are sequentially performed,
wherein, in the case of sensing a reducing gas, the reading preparation step of applying a positive pre-bias voltage; pulse and the reading step of applying a read-bias voltage pulse are sequentially performed, and
wherein, in the heating step and the reading preparation step, a voltage between the drain and the source is maintained at 0 V.

16. The pulse operating method according to claim 12,
wherein a step of sequentially performing the reading step and the heating step is repeated once or more times, and
wherein, in the heating step, a voltage between the drain and the source is maintained at 0 V.

17. The pulse operating method according to claim 12,
wherein the heat-bias voltage pulse of the heating step and the pre-bias voltage pulse of the reading preparation step are applied so that at least portions thereof overlap with each other, and the read-bias voltage pulse of the reading step is applied, or the neat-bias voltage pulse and the read-bias voltage pulse of the heating step are applied so that at least portions thereof overlap with each other, and
wherein, in the heating step and the reading preparation step, a voltage between the drain and the source is maintained at 0 V.

18. The pulse operating method according to claim 12,
wherein the heating step is performed before the reading preparation step and the reading step,
wherein the heating step and the reading step are sequentially performed, or the heating step, the reading preparation step, and the reading step are sequentially performed, and
wherein, in the heating step and the reading preparation step, a voltage between the drain and the source is maintained at 0 V.

19. The pulse operating method according to claim 18,
wherein a step of sequentially performing the heating step and the reading step or a step of sequentially performing the heating step, the reading preparation step, and the reading step is repeated twice or more times.

* * * * *